United States Patent
Danz et al.

(10) Patent No.: US 10,281,321 B2
(45) Date of Patent: May 7, 2019

(54) ARRANGEMENT FOR SPATIALLY RESOLVED AND WAVELENGTH-RESOLVED DETECTION OF LIGHT RADIATION EMITTED FROM AT LEAST ONE OLED OR LED

(71) Applicant: FRAUNHOFER-GESELLSCHAFT ZUR FOERDERUNG DER ANGEWANDTEN FORSCHUNG E.V., Munich (DE)

(72) Inventors: Norbert Danz, Jena (DE); Christoph Waechter, Jena (DE)

(73) Assignee: FRAUNHOFER-GESELLSCHAFT ZUR FOERDERUNG DER ANGEWANDTEN FORSCHUNG E.V., Munich (DE)

( * ) Notice: Subject to any disclaimer, the term of this patent is extended or adjusted under 35 U.S.C. 154(b) by 215 days.

(21) Appl. No.: 15/329,096

(22) PCT Filed: Jul. 10, 2015

(86) PCT No.: PCT/EP2015/065834
§ 371 (c)(1),
(2) Date: Jan. 25, 2017

(87) PCT Pub. No.: WO2016/012276
PCT Pub. Date: Jan. 28, 2016

(65) Prior Publication Data
US 2017/0248463 A1    Aug. 31, 2017

(30) Foreign Application Priority Data

Jul. 25, 2014 (DE) .................. 10 2014 214 721

(51) Int. Cl.
*H05B 33/00* (2006.01)
*G01J 1/42* (2006.01)
(Continued)

(52) U.S. Cl.
CPC ............... *G01J 1/4228* (2013.01); *G01J 3/10* (2013.01); *G01J 3/42* (2013.01); *G01J 3/505* (2013.01);
(Continued)

(58) Field of Classification Search
CPC ........ H05B 33/00; H05B 33/02; H05B 33/06; H05B 33/14
(Continued)

(56) References Cited

U.S. PATENT DOCUMENTS 5,478,658 A * 12/1995 Dodabalapur ...... H01L 51/5265
313/504
5,780,174 A    7/1998 Tokito et al.
(Continued)

FOREIGN PATENT DOCUMENTS

DE    102006039171 A1    2/2008
DE    102009037185 A1    12/2010
(Continued)

*Primary Examiner* — Kevin K Pyo
(74) *Attorney, Agent, or Firm* — Jacobson Holman, PLLC.

(57) ABSTRACT

The invention relates to an arrangement for a spatially resolved and wavelength-resolved detection of light radiation emitted from at least one OLED or LED. A multilayer system is arranged between an electrode, an OLED or an LED, and a substrate and is formed using layers formed alternately above one another from a material having higher and lower optical refractive indices n. In this respect, light radiation from the at least one OLED or LED and having a plurality of different wavelengths $\lambda_1, \lambda_2, \lambda_3, \ldots \lambda_n$ thus exits the multilayer system. Light radiation that exits at different wavelengths $\lambda_1, \lambda_2, \lambda_3, \ldots \lambda_n$ at different angles is incident onto at least one detector array after at least a simple refraction at an optical element or after reflection at a layer or at a layer system of a sensor such that light radiation at a wavelength $\lambda_1, \lambda_2, \lambda_3, \ldots$ or $\lambda_n$ is incident (Continued)

Figure 3B:
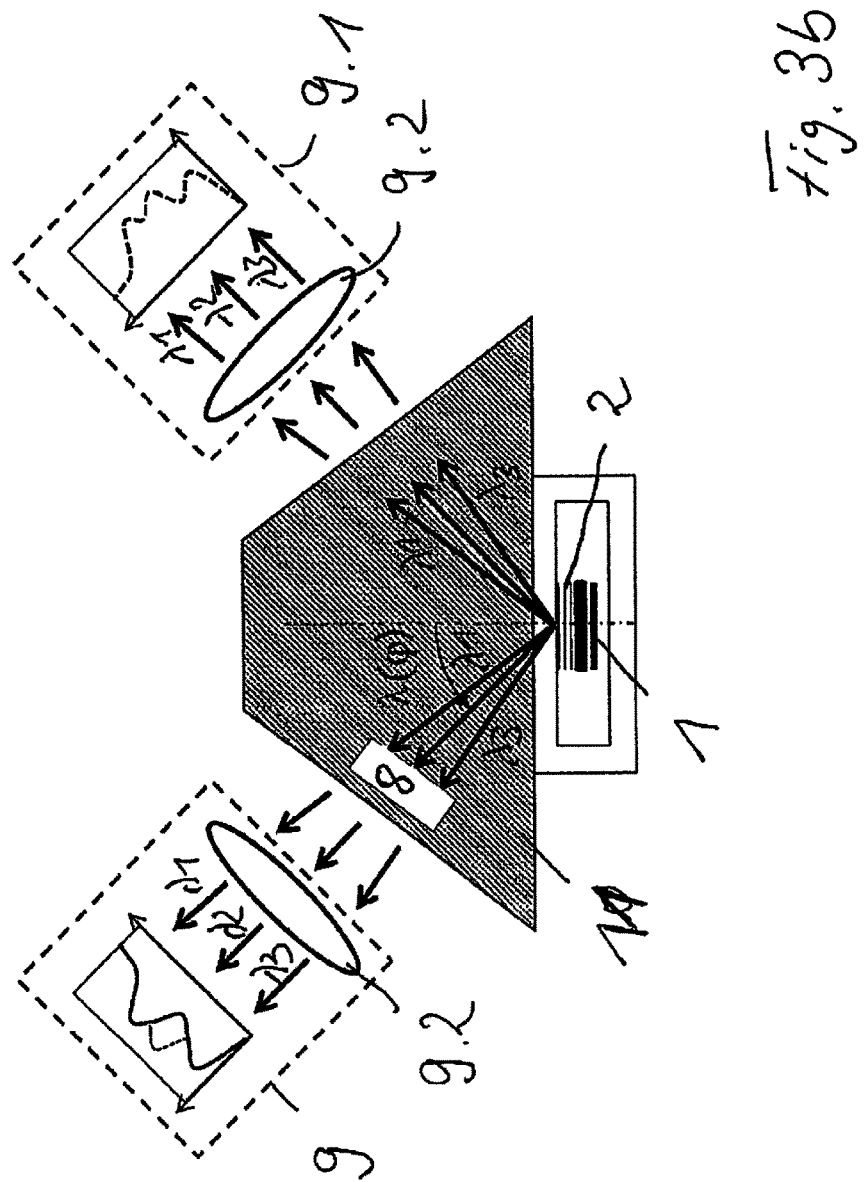

onto a respective detector element of the detector array. The detector elements of the detector array are arranged discretely from one another.

6 Claims, 14 Drawing Sheets

(51) Int. Cl.
| | |
|---|---|
| *G01J 3/10* | (2006.01) |
| *G01J 3/42* | (2006.01) |
| *G01J 3/50* | (2006.01) |
| *G01N 21/552* | (2014.01) |
| *H01L 51/50* | (2006.01) |
| *H01L 51/52* | (2006.01) |
| *H01L 33/10* | (2010.01) |
| *H01L 33/58* | (2010.01) |

(52) U.S. Cl.
CPC ......... *G01N 21/553* (2013.01); *H01L 33/105* (2013.01); *H01L 33/58* (2013.01); *H01L 51/5036* (2013.01); *H01L 51/5265* (2013.01); *H01L 51/5275* (2013.01); *G01J 2001/4252* (2013.01); *G01N 2201/0628* (2013.01)

(58) Field of Classification Search
USPC .......................................... 313/500, 504, 506
See application file for complete search history.

(56) References Cited

U.S. PATENT DOCUMENTS

| | | |
|---|---|---|
| 7,489,074 B2 | 2/2009 | Antoniadis et al. |
| 2004/0140757 A1* | 7/2004 | Tyan .................. H01L 51/5265 313/504 |
| 2007/0291805 A1 | 12/2007 | Ledentsov |
| 2012/0181920 A1 | 7/2012 | Frischelsen et al. |

FOREIGN PATENT DOCUMENTS

| | | |
|---|---|---|
| DE | 102012109135 A1 | 3/2014 |
| EP | 1739764 A2 | 1/2007 |
| JP | 2012204240 A | 10/2012 |
| WO | WO2010/060915 A2 | 6/2010 |
| WO | WO2014/181695 A1 | 11/2014 |

* cited by examiner

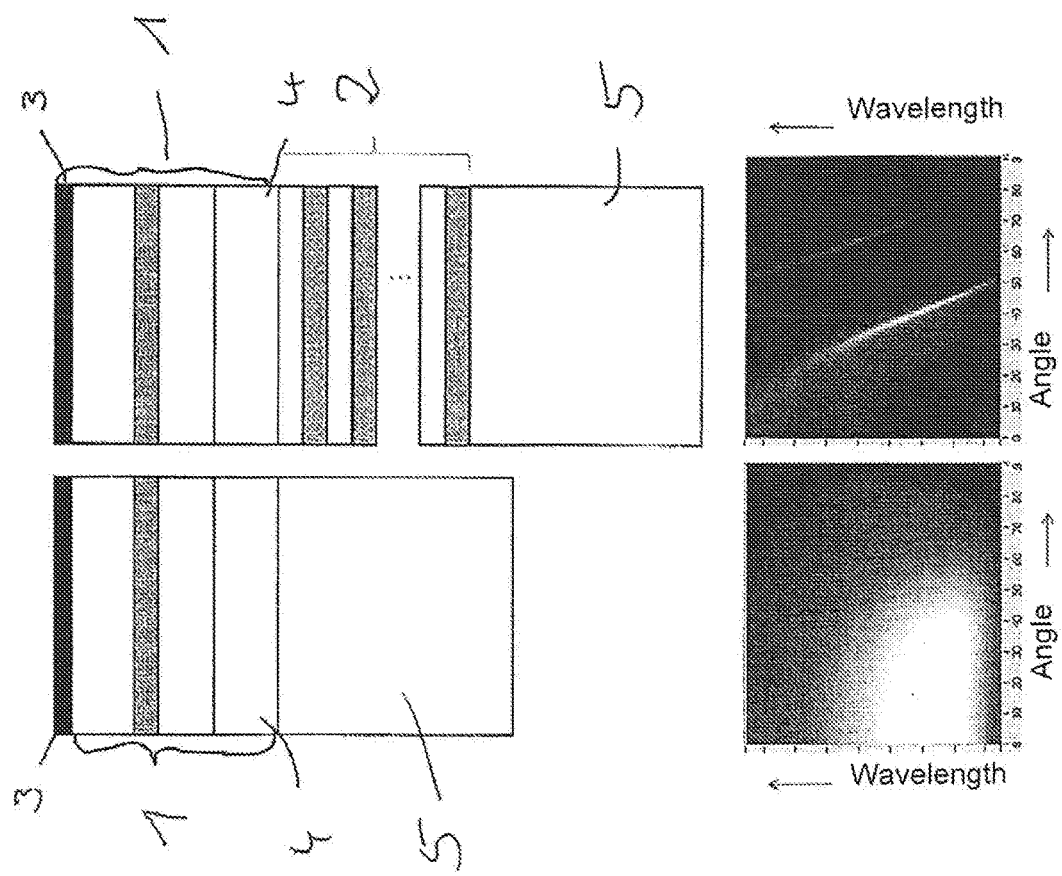

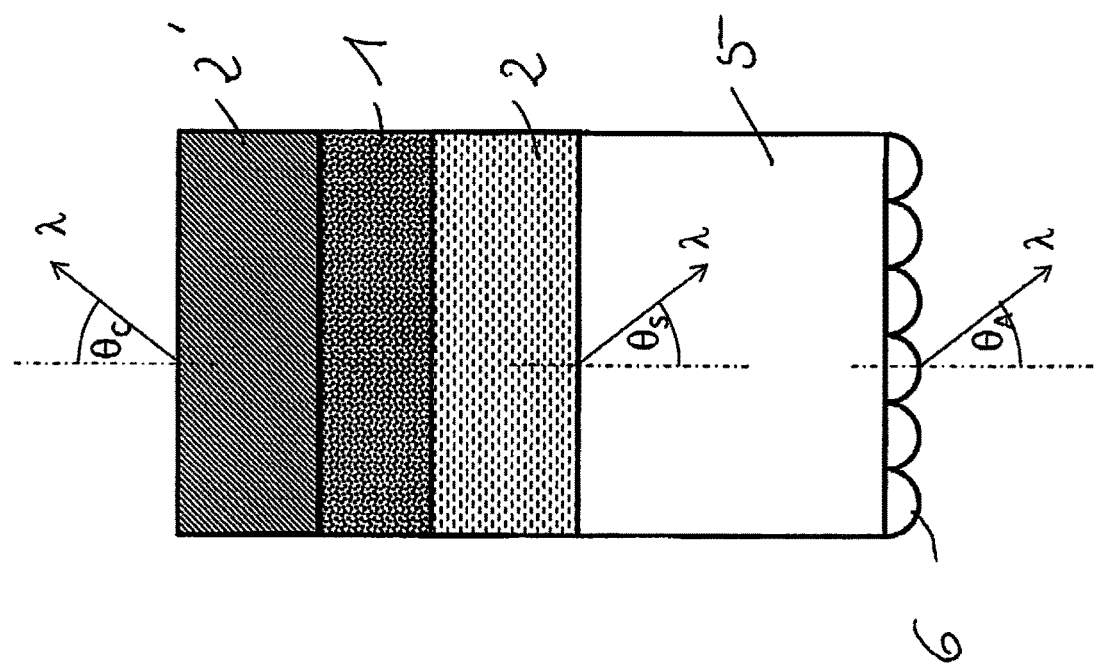

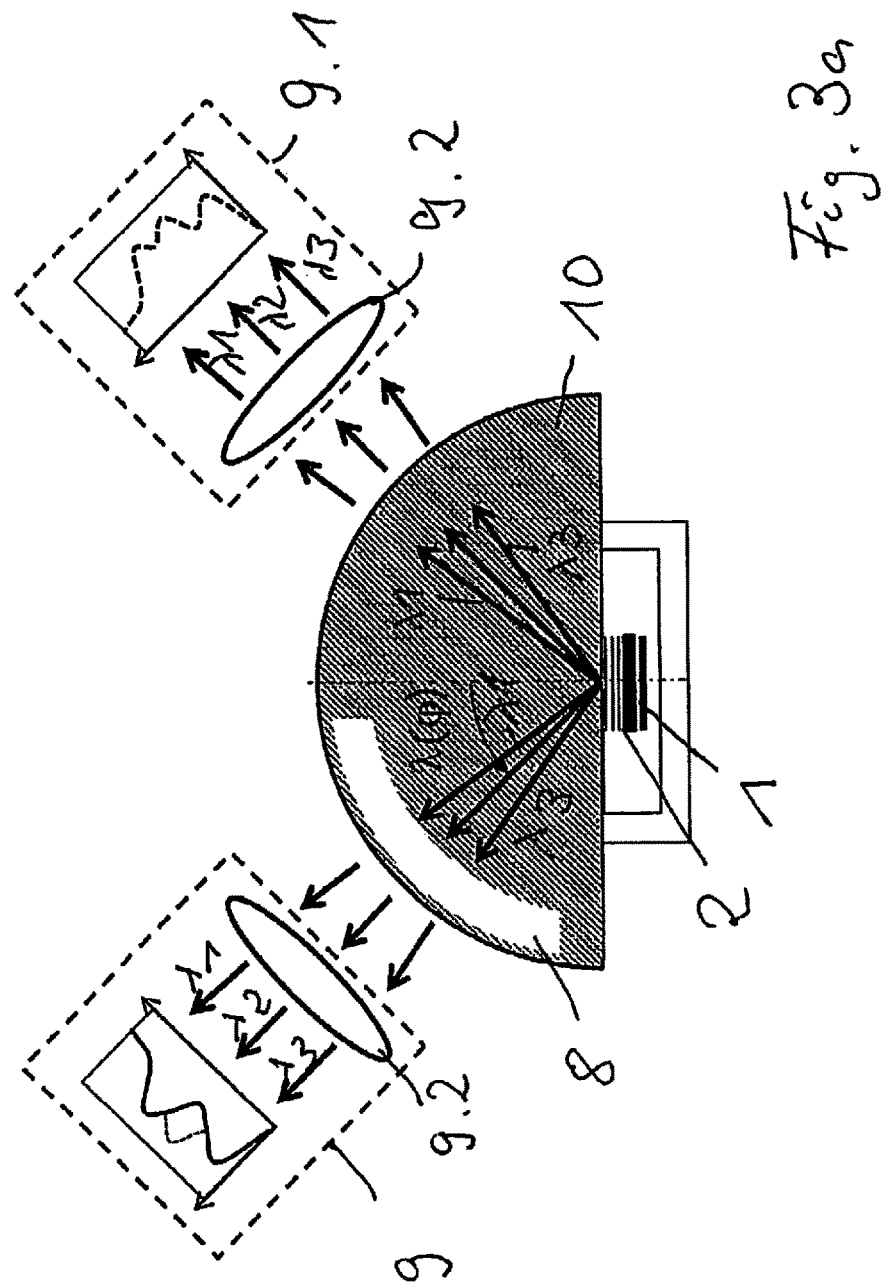

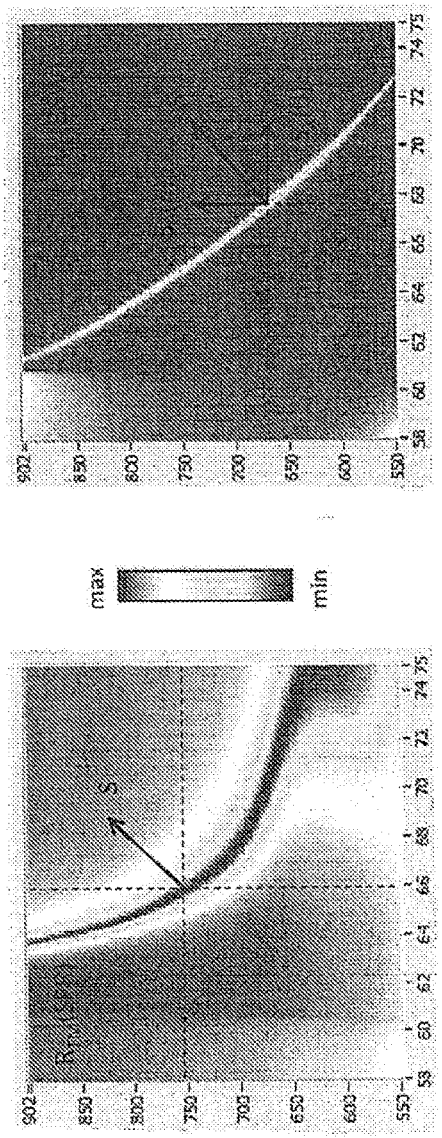
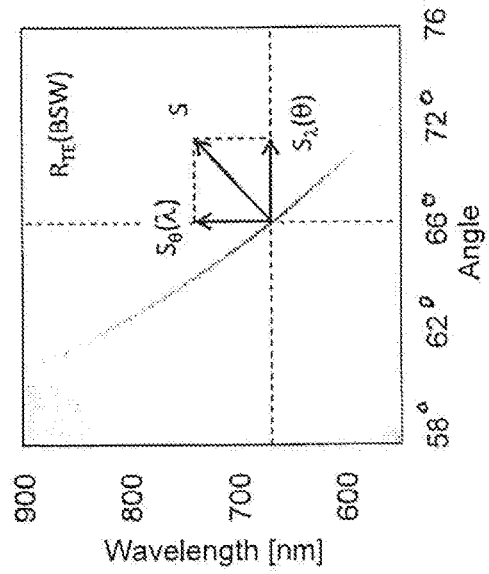
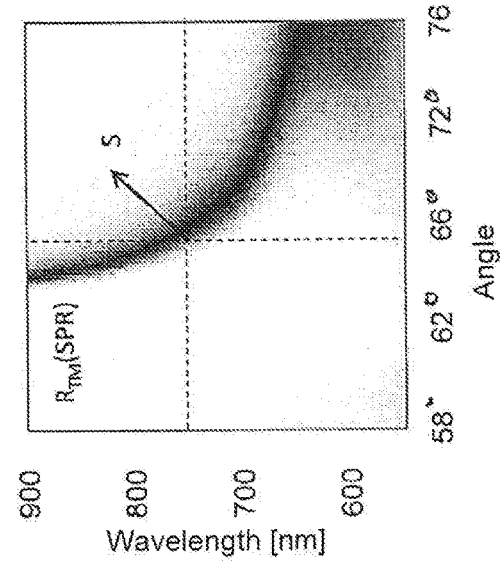
Fig. 4

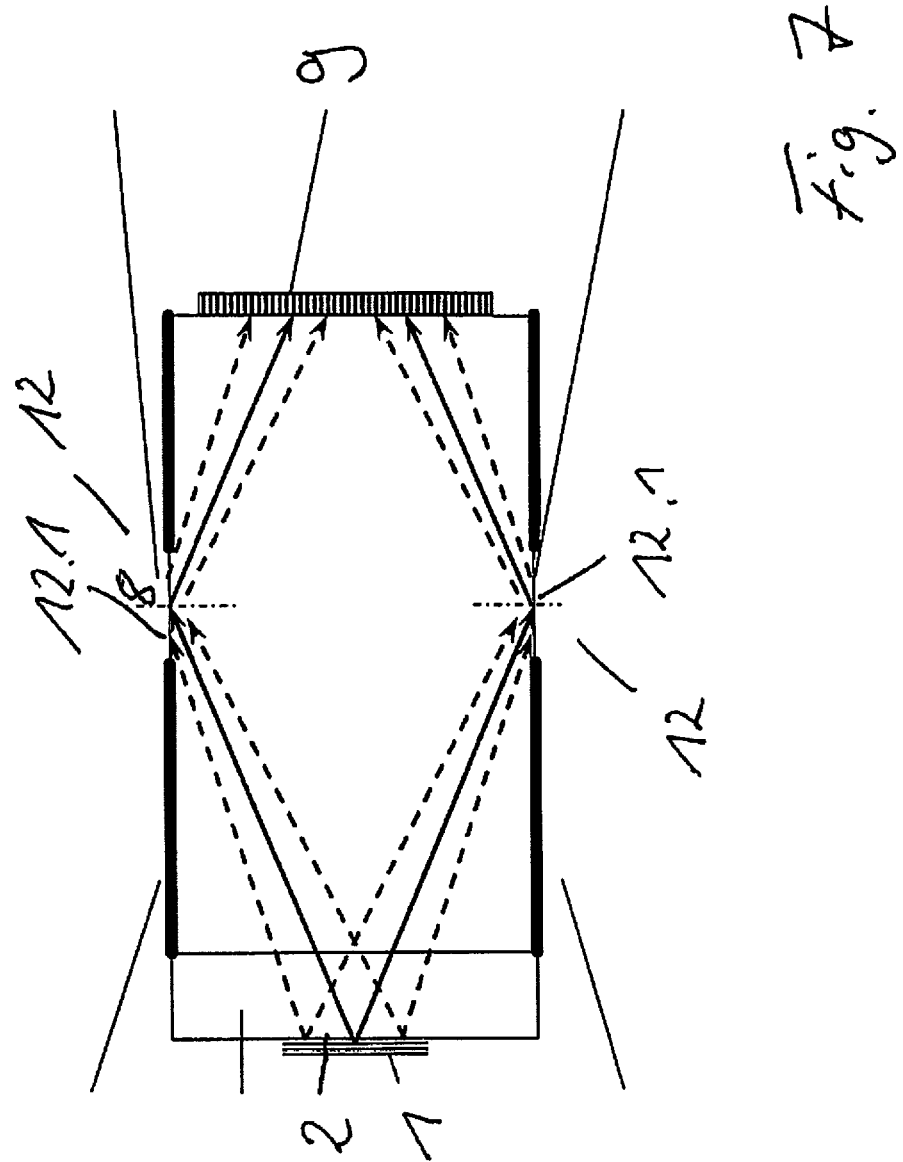

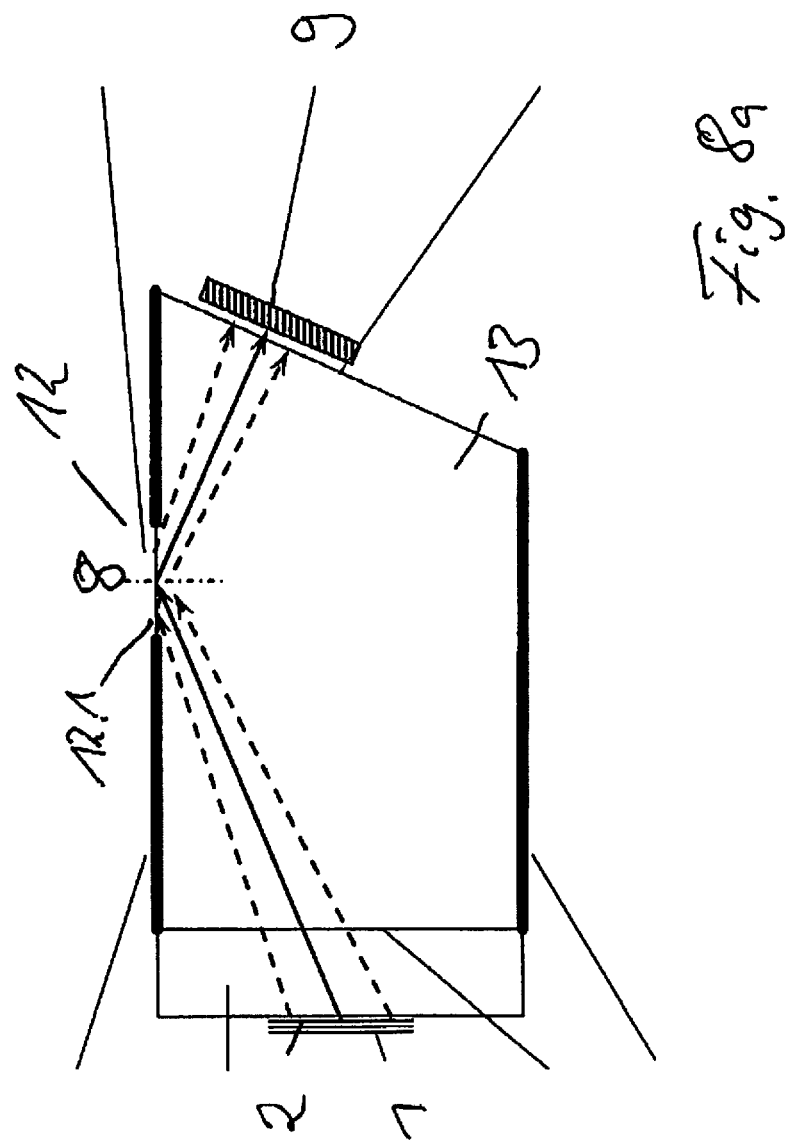

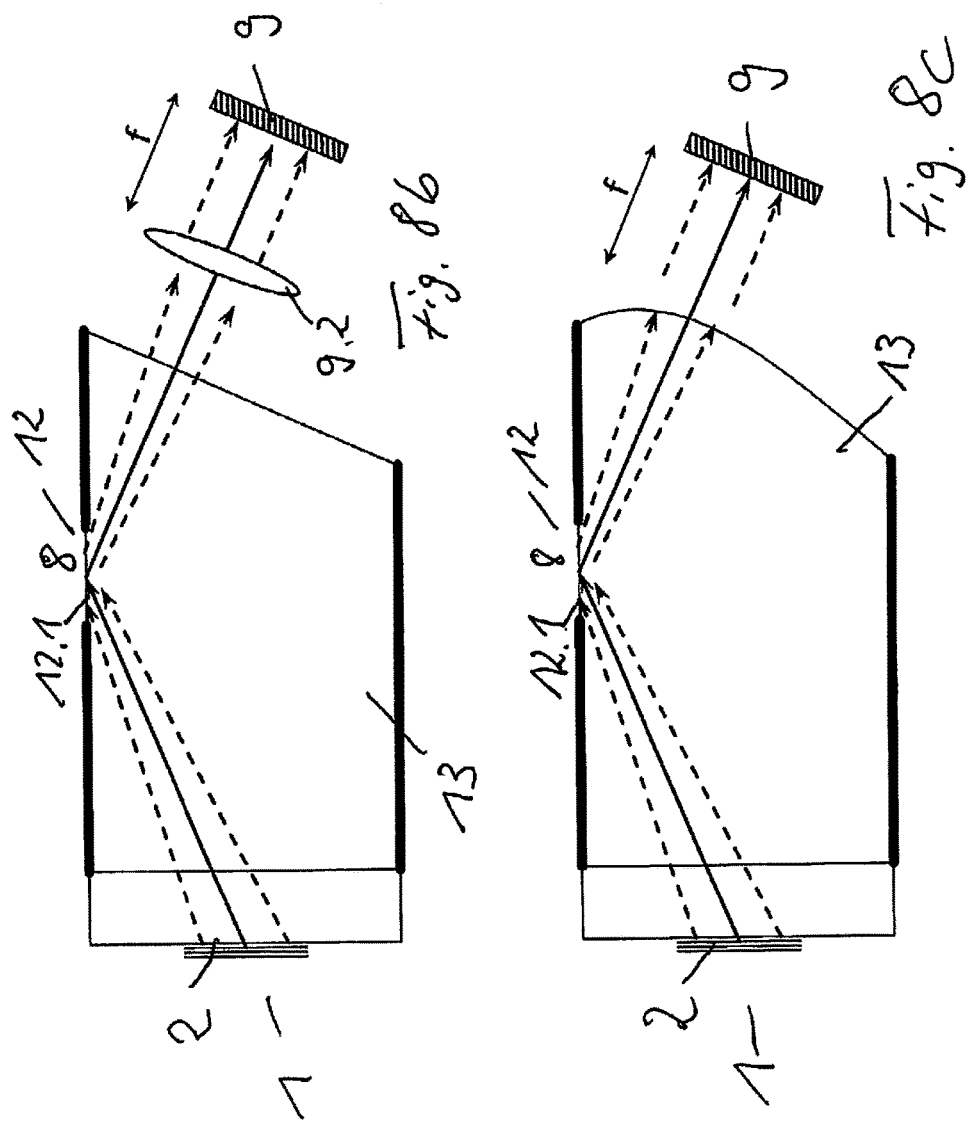

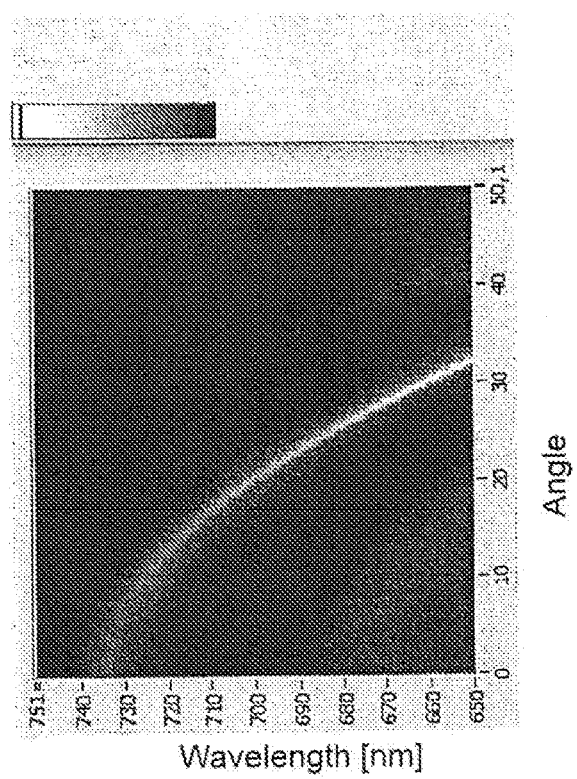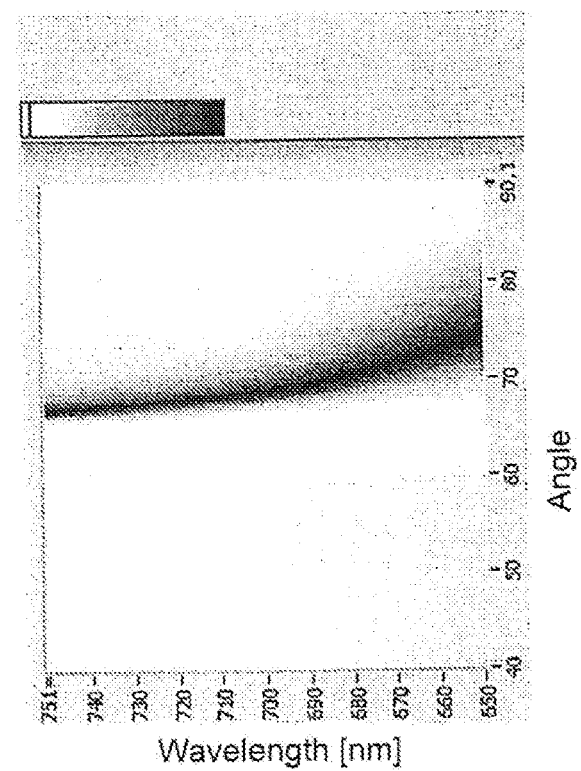
Fig. 9

ARRANGEMENT FOR SPATIALLY RESOLVED AND WAVELENGTH-RESOLVED DETECTION OF LIGHT RADIATION EMITTED FROM AT LEAST ONE OLED OR LED

The invention relates to an arrangement for a spatially resolved and wavelength-resolved detection of light radiation emitted from at least one OLED or LED. At least one sample can be analytically inspected in this process.

It should be noted in this respect that a defined dispersion of the emission (i.e. spectral angle dependence) can be imprinted using a light source emitting spontaneously and over a broad band such that it can be used without a classical spectral apparatus for spectroscopic inspections.

In particular LEDs or OLEDs can be considered for this purpose. It is specifically the goal for OLEDs or LEDs to influence the Lambertian radiation field of these light sources such that the OLEDs or LEDs are qualified as metrological light sources.

No solution has previously been known for this problem. A classical (point) light source can naturally obviously be combined with a monochromator. It would alternatively be possible also to integrate the function of this monochromator into a (complex) optical element and to combine it with a classical light source. In this respect, however, intensity losses occur and it is only possible to work with one wavelength or with a very limited wavelength spectrum.

OLEDs and LEDs have been developed into commercial light sources over the past ten years. In this respect, the use of OLEDs is substantially restricted to displays in small dimensions for mobile radio units and in large formats as TVs and to general lighting. Efficient construction elements in the range of 60 ... 80 lm/W are available for this purpose. They have, however, not yet become established on the market. In addition, backlights or self-illuminating signs are named as areas of application. As the market introduction of OLEDs progresses, other applications—differing from the two named above—will also become interesting in future. In this respect, the focus will normally be on the homogeneity of the radiation field (over the surface or over the angle of the emitted radiation).

Since the (academic) availability of OLEDs, they have also been used for sensory work. The aim of this work is a far-reaching integration of the light source and the optical sensor. In this respect, organic photodetectors have also been proposed in some cases to allow a complete integration of the optical system. Organic photodetectors, however, present additional technological demands and risks. They limit the performance of such systems due to the ratio of measured signal to substrate (signal-to-noise ratio) that is poorer in comparison with inorganic detectors. The use of OLEDs as a light source can take place in different manners. They are in many cases used for fluorescence excitation, with a "sandwich" of light source, sample, filters and detector typically being put together. The large angle spectrum of the emitted radiation is problematic in this respect. Light radiation having the respective wavelengths of the emitted spectrum is in this respect emitted in the most varied undefined directions.

The service life based systems in which only the decay time of a sensor dye is evaluated have a special role in the fluorescence approaches. In particular SPR is described in the literature with respect to measurement approaches free of markings. In this respect, the broad (angle) spectrum of the emission is also restricted here by a fiber or also by additional microscopic elements. A specific modification of the radiation field to achieve the ideal characteristics of the light source for the (marking-free) sensor system is not known.

It is therefore the object of the invention to provide possibilities with which the light radiation can be emitted with wavelength resolution at defined angles with OLEDs or LEDS emitting light radiation in a broad band and said light radiation can be used in a wavelength-specific manner for the sensor determination of measured signals.

This object is achieved in accordance with the invention by an arrangement having the features of the claims set forth herein.

In the arrangement in accordance with the invention for a spatially resolved and wavelength-resolved detection of light radiation that is emitted by at least one OLED or LED, a multilayer system is present between an electrode of an OLED or of an LED that is formed using layers formed alternately above one another from a material having a higher and a lower optical refractive index n and from a substrate. Light radiation having a plurality of different wavelengths $\lambda 1, \lambda 2, \lambda 3, \ldots \lambda n$ is emitted from the at least one OLED (1) or LED and thus exits the multilayer system such that light radiation having different wavelengths $\lambda 1, \lambda 2, \lambda 3, \ldots \lambda n$ exits at defined angles, with the light radiation dispersed in a defined manner by means of the multilayer system being incident onto at least one detector array configured for the spatially resolved detection of light radiation after at least simple refraction at an optical element or after reflection at a layer or at a layer system of a sensor. In this respect, a simple optical refraction takes place when the emitted light radiation exiting the multilayer system exits an optical element that is arranged directly above the multilayer system. That is, the multilayer system is formed directly on a surface of an optical element or the optical element is optically coupled thereto by means of an immersion fluid.

This spatially resolved detection results in a wavelength-resolved measurement due to the fact that the different wavelengths $\lambda 1, \lambda 2, \lambda 3, \ldots \lambda n$ are emitted at different angles.

In this respect, the respective multilayer system can be configured such that light radiation having a larger wavelength exits at a larger angle with respect to the normal of the surface of a substrate of an OLED or of an LED than light radiation having a smaller wavelength, or vice versa. In this respect, a dependence of the angles on the respective wavelengths can be observed so that the angles having wavelengths that become smaller or longer are respectively varied in accordance with the desired wavelengths varying in an analogous manner.

An optical element at which an optical refraction takes place can be an optical lens or a prism. Such an optical element can be an integral component of a substrate of the OLED or of the LED, can be connected to the substrate by means of an immersion fluid or can be arranged at a spacing from the substrate with a gap present therebetween.

An optical element can, however, also be formed on the surface of the substrate at which the light radiation emitted by an OLED or LED exits or can be present there as a microscopic surface structure. A further-reaching dispersion, preferably a spreading of the light radiation at the different wavelengths $\lambda 1, \lambda 2, \lambda 3, \ldots \lambda n$ can thus be achieved such that the spacings of positions of incidence can be increased, in particular on individual detectors of the detector array.

The detector array should be arranged and/or configured such that light radiation having a specific wavelength $\lambda 1, \lambda 2, \lambda 3, \ldots$ or $\lambda n$ is incident on a respective at least one correspondingly arranged defined detector element (pixel)

of the detector array with which the respective intensity of light radiation of known wavelengths can be measured. In this respect, light radiation of a wavelength λx can be incident on a single detector element and the intensity of the light radiation can thus be determined for this wavelength λx using the one detector element. This can be achieved for a wavelength λx, but also using a group of detector elements arranged next to one another that are arranged correspondingly close enough to one another and nevertheless such that no light radiation having different wavelengths is incident onto these detector elements. A group of detector elements can, for example, also be an arrangement of detector elements in a row.

Since the radiation field of an OLED or LED proposed as a light source here is (rotationally) symmetrical to the surface normal of the light source, a second optical path having a second detector array can be used that is then preferably usable for a reference measurement. This equally allows the simultaneous measurement of a plurality of samples. In this respect, the arrangement of a sample in the optical path of the light radiation split in a dispersive manner into a plurality of wavelengths at different angles or also at an SPR or BSW sensor can be dispensed with in the reference measurement. Two detector arrays should be arranged with angular symmetry with respect to an axis or plane.

SPR sensors or BSW sensors already known per se can be used in the invention. At least one SPR sensor or BSW sensor can be present in the invention having a film or a thin film system at which the light radiation having the different wavelengths λ1, λ2, λ3, . . . λn is reflected and is then directed to a detector array.

The active electrical system of an OLED or of an LED remains unchanged due to the arrangement of a dielectric multilayer system, that is, of a system of optically high-refractive and low-refractive layers that are arranged above one another and between the substrate transparent for the light radiation and a surface emitting light radiation (e.g. the anode). An optical cavity is thereby formed that can be formed by the (metallic) cathode on the one side and the dielectric layer stack on the other side with an OLED.

With an LED or OLED that has two electrodes transparent for the emitted light radiation, a second multilayer system can be used by which light radiation emitted by this electrode can likewise be directed onto at least one further detector array, as described above. The second multilayer system can be configured like the first multilayer system. It can, however, also be formed from different materials for the optically higher and optically lower refractive layers and/or using layer thicknesses of the individual layers forming the second multilayer system differing from the first multilayer system in comparison with those of the first multilayer system through which light radiation exits that is emitted by the respective other electrode. With two differently configured multilayer systems that are used at the same light source, a different dispersion at which light radiation of different wavelengths λx can be emitted at different angles can then be used. This can then simultaneously be used for different inspections, for example for different analyses at different samples or at the same samples.

There is the possibility with the invention to direct the emitted light radiation onto a detector array through a sample at least partly transparent for the light radiation. The sample can in this respect preferably be liquid and can contain analytes to be detected.

The invention will be explained in more detail in the following with reference to examples. In this respect, technical features of different examples can also be used in other examples independently of the respective example in which they are described.

Figure 5:
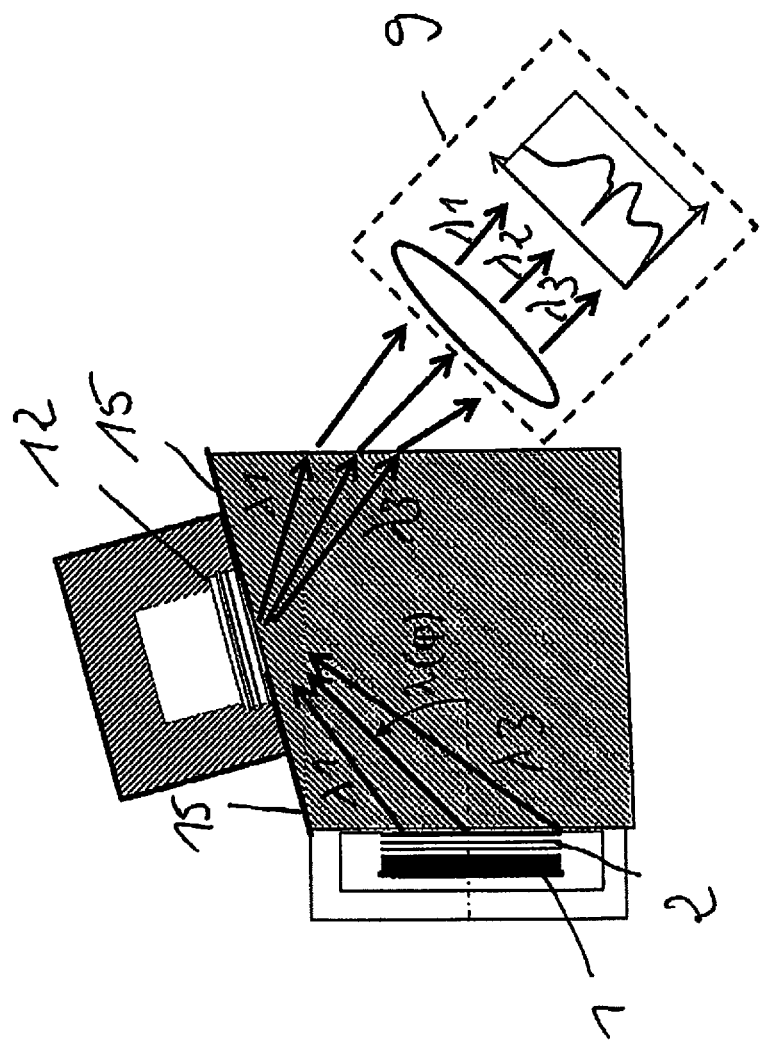
Figure 6:
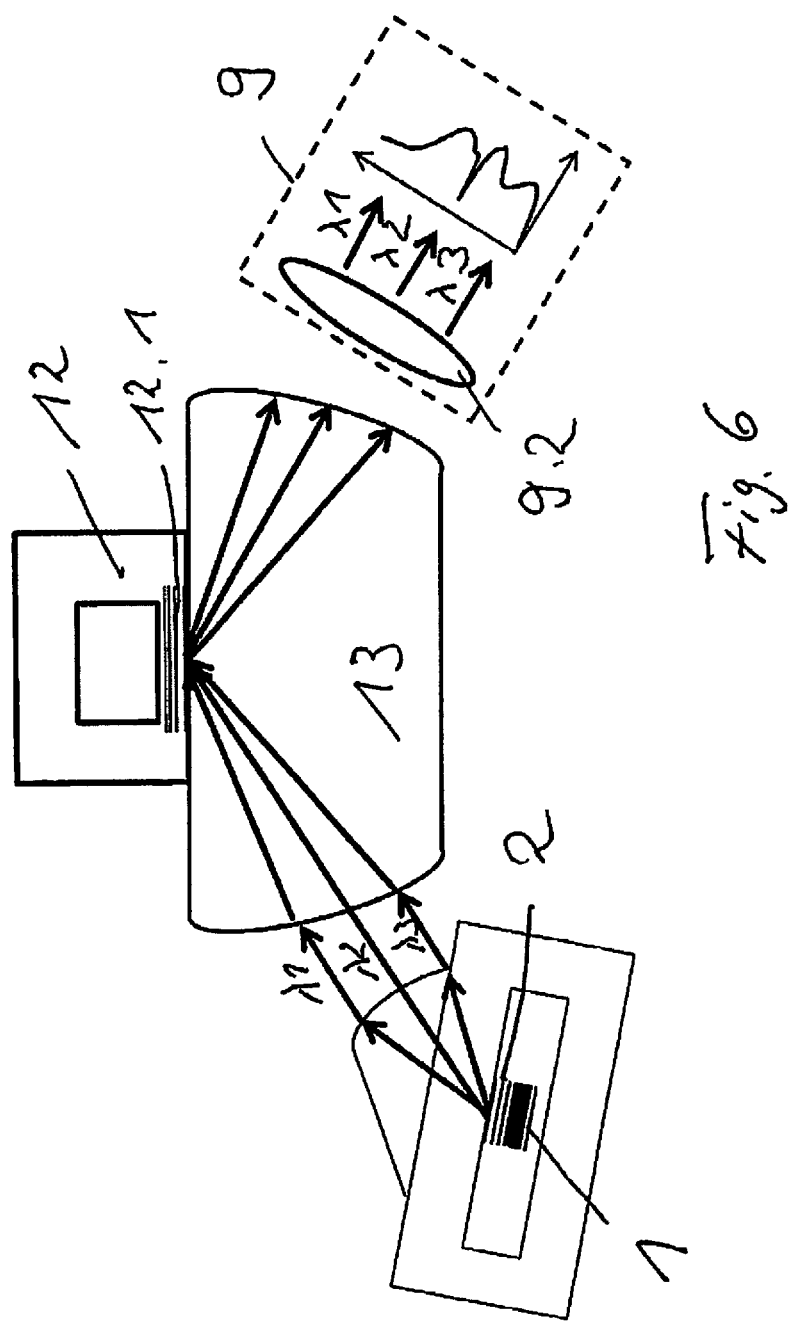
Figure 10:
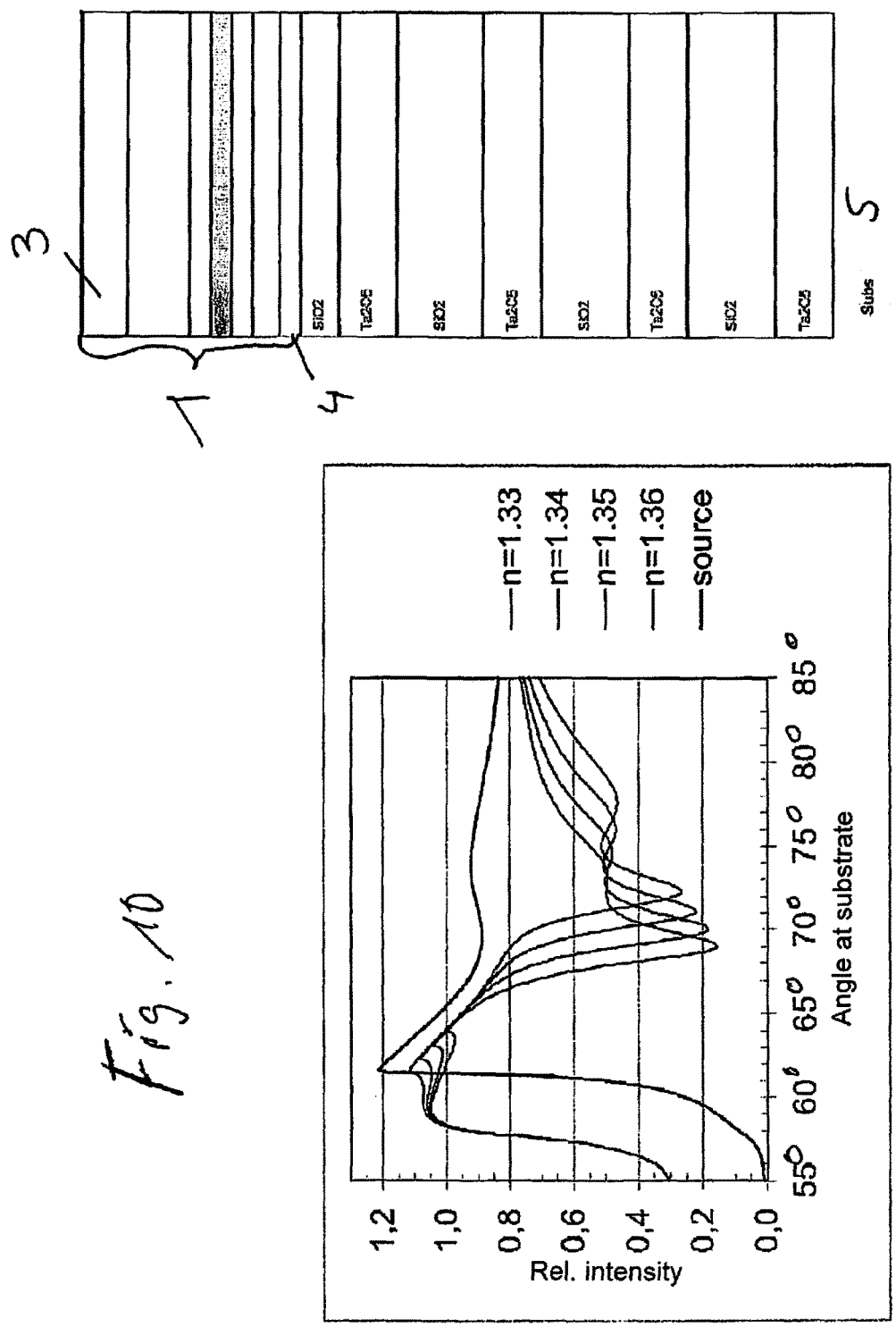
Figure 11:
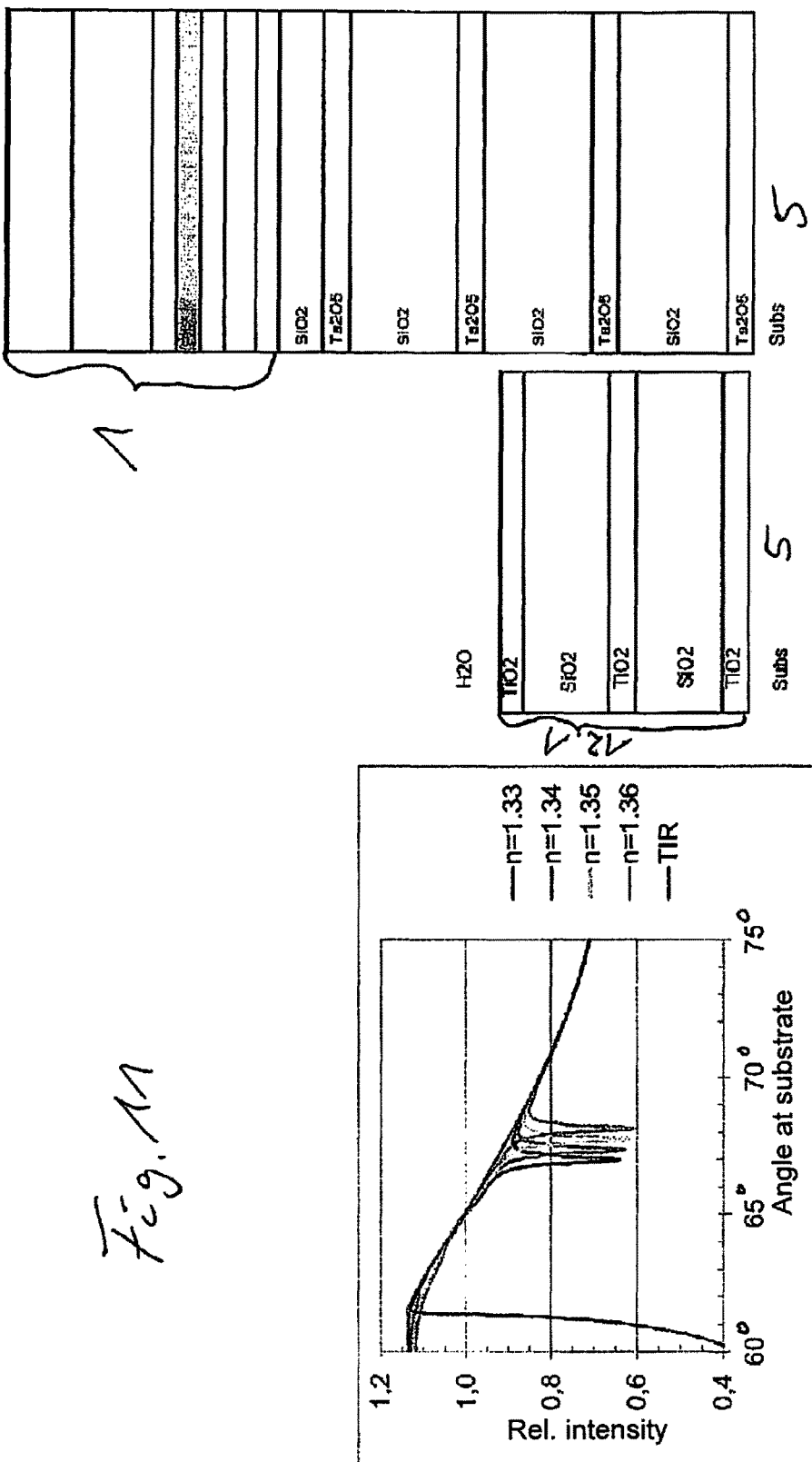
Figure 12:
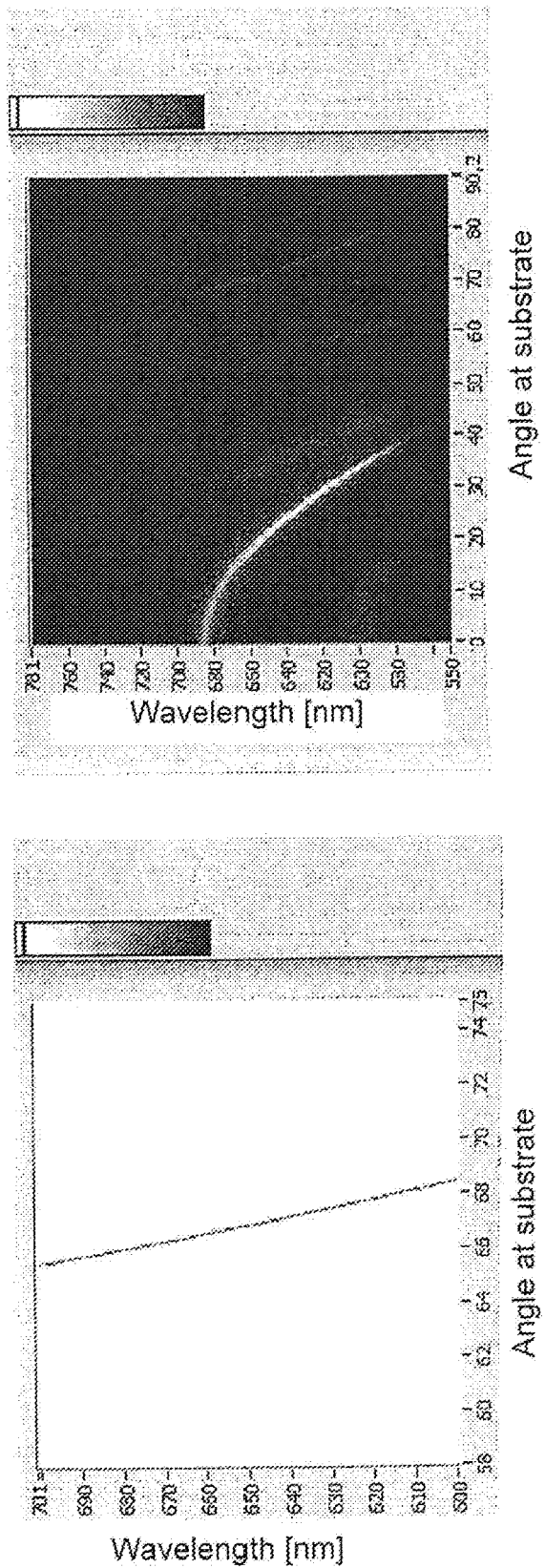

There are shown:

FIG. 1 in schematic form, an example of a conventional OLED and an example using a multilayer system as well as images of angles that are varied in dependence on the respective wavelength and at which light beams can be emitted;

FIG. 2 in schematic form, an example of an OLED with a multilayer system and a microscopic surface structure at a substrate;

FIGS. 3a and b examples of an arrangement in accordance with the invention with a respective optical element at which a refraction of emitted and dispersed light radiation takes place;

FIG. 4 images of dispersed light radiation after a reflection at an SPR sensor (left) and at a BSR sensor (right);

FIG. 5 an example in a schematic representation in which dispersed light radiation from an OLED enters into a body transparent for the light radiation, the body being a component of an SPR or BSW sensor and having surfaces influencing the beam guidance;

FIG. 6 an illustration with dependencies of the angles at which light radiation exits the substrate of an OLED in dependence on its respective wavelength (left), enters into a substrate with an SPR or BSW sensor (middle), and is detected by a detector having an optical element (right);

FIG. 7 an example of an arrangement in accordance with the invention with two SPR sensors whose layers are irradiated with dispersed light radiation that has been emitted from an OLED having a multilayer system and where light radiation reflected from this, that is still dispersed, is directed to a detector array for a spatially resolved measurement, with the SPR sensor arranged at the bottom being able to form a reference without a sample or with a known sample;

FIGS. 8a-c examples for possible embodiments of an arrangement in accordance with the invention with an SPR sensor or BSW sensor;

FIG. 9 diagrams of the dependence of angles of dispersed light radiation that exits the light source into a substrate (right) and the reflection from the substrate (left) with an SPR sensor;

FIG. 10 in a schematic illustration, the design of an OLED usable in the invention with a multilayer system that can be used in conjunction with an SPR sensor (e.g. in accordance with FIG. 6, 7, or 8) and a diagram of the relative intensities detectable by a detector in dependence on angles of the dispersed light radiation at a substrate at different optical refractive indices of an aqueous solution to be inspected as the sample;

FIG. 11 in schematic form, an example of an OLED with a multilayer system that can be used with a BSW sensor that has a layer system such as is likewise shown (e.g. in accordance with FIG. 6, 7 or 8) and a diagram of the relative intensities detectable by a detector in dependence on angles of the dispersed light radiation at a substrate with different optical refractive indices of an aqueous solution to be inspected as the sample; and FIG. 12 diagrams of the dependence of angles of dispersed light radiation that exits the light source into a substrate (right) and the reflection from the substrate (left) with a BSW sensor.

FIG. 1 shows by way of example a "normal" OLED 1 as well as an OLED 1 having a dielectric multilayer system 2. The light emission can be dramatically varied by the introduction of the multilayer system 2 at which layers having smaller and larger optical refractive indices are arranged stacked above one another. An almost linear relationship between the emitted wavelengths and the angles is obtained in the example in which light radiation having different angles is emitted, by way of example, in dependence on wavelength $\lambda 1, \lambda 2, \lambda 3$. In this respect, the multilayer system 2 is formed between the anode 4 and the substrate 5 of the OLED. In a form not shown, a multilayer system can be arranged at the cathode side of the OLED in addition to the multilayer system at the substrate side to influence the radiation field analogously. The cathode 3 in this case has to be composed of a material sufficiently transparent for the respective emitted light radiation. Such an embodiment can be used for simultaneous different measurements or for the carrying out of a reference measurement. The two multilayer systems 2 do not have to be identical. Wavelengths that are respectively the same and each have different angles can thus be emitted using the multilayer systems 2 so that, for example, a wavelength $\lambda 1$ exits one multilayer system 2 at the angle $\theta 1$ and exits the other multilayer system at the angle $\theta 2$, with these angles being of different amounts.

The properties of the radiation field of the emitted radiation depend on the following parameters:

emission spectrum of the emitter(s) used in the OLED or in the LED spacing of the emitters from the cathode (thickness of the ETL layer)

properties of the dielectric multilayer system

A microcavity can be built up by the design of the layer stack of an OLED 1 in conjunction with the dielectric multilayer system 2 such that the very wide and Lambert-like radiation field of the "normal" OLED (bottom left of FIG. 1) is dramatically modified. It becomes clear in FIG. 1 (bottom right) that the emission of light radiation takes place along a curve in the angle/wavelength plane. The wavelength of the emission is thereby linked to the angle due to the dispersion of the multilayer system 2 in the microcavity in conjunction with the corresponding multilayer system.

FIG. 2 shows the generalized structure of such an OLED as a light source. As already mentioned, in this respect a multilayer system 2' can be arranged both at the substrate side (analog to FIG. 1) and at the cathode side to directly modify the emission properties. Both multilayer systems 2 and 2' naturally have to consider, or may not interfere with, the electric function and the optical properties, in particular the spectrum of the respective emitted light radiation, of the OLED 1.

For the application, either the emitted radiation field
 in the substrate can then be influenced in the substrate, e.g. via the immersion coupling with a semisphere/semi-cylinder or the like (cf. FIG. 3), or
 in air (substrate side), optionally after the decoupling by a microscopic structure
 in air (cladding side).

In FIG. 2, a microoptical surface structure 6 is now present or is configured at a surface of the substrate 5 by which the exiting light radiation having the wavelengths $\lambda 1$, $\lambda 2$, $\lambda 3$ can be additionally influenced with respect to its exit angle by optical refraction. An additional angular spread can thus be achieved. A microscopic surface structure 6 can thus comprise miniaturized optical elements (e.g. lenses, pyramids, cones) or also dispersing structures.

Such an emission at both sides can also be used for reference purposes. The active system can include one or more emitters (OLEDs or LEDs) for light radiation, with the spatial arrangement of the emitters also being able to be set in the entire layer stack to influence the angles of the emitted light radiation.

The invention can be used in all areas in which spectroscopic measurements are to take place. In this respect, however, preferred regions are to be named in which in-situ measurements are carried out due to their potential for miniaturization. This applies to biochemical analysis for environmental diagnostics, food diagnostics, veterinary diagnostics and human diagnostics and can naturally be expanded to regions of chemical analysis and many more.

In this sense, two specific applications will be described in the following. The combination with the above-described optical design with an OLED represents a new advantageous technological approach.

An application of such an OLED 1 is shown in FIGS. 3*a* and 3*b*. In this respect, the fact is exploited that different spectral components of the light radiation are emitted into the substrate 5 of the OLED 1 at different angles. If now a liquid 8 to be analyzed (as the sample) is introduced into this (limited) irradiated angular range, light radiation having different wavelengths thus transmits at different positions.

This transmission can be measured by a direct arrangement of a CCD or CMOS camera 9 after transmission through the liquid 8. It is also possible to complement the camera 9 with an objective 9.2 focused on "infinity". It is possible on the basis of the symmetry of the OLED irradiation field to carry out a reference measurement of the emitted spectrum using a further camera 9.1 offset by 180° (that is in the opposite emission direction) and thus to correct the measured values.

As becomes clear from the two representations of FIGS. 3*a* and 3*b*, the passage conducting the liquid 8 (sample) can be arranged on a semi-cylinder/semisphere (FIG. 3*a*) 10 or on a surface of an optical prism 11 (FIG. 3*b*). The first-named possibility has the advantage that fewer optical refraction effects occur at the interfaces. The prism 11 is easier to manufacture from a technological aspect, with the law of optical refraction having to be taken into account at the different interfaces in dependence on the wavelength range and angular range.

Glass or also polymer can be used as the material of the semisphere/semi-cylinder/prism 10, 11. The OLED 1 can be deposited directly onto this material or can be coupled thereto by immersion fluid. Depending on the design of the OLED 1, an air gap can also be arranged between the substrate 5 of the OLED 1 and the semisphere/semi-cylinder/prism 10, 11 with the sample 8.

The sensors can be understood by way of example as SPR sensors (surface plasmon resonance) or BSW sensors (Bloch surface waves) 12. These sensors 12 are based on the observation of the "resonance" that is observed on the reflection at a thin film of metal (SPR) or at dielectric layers (BSW) 12.1. This resonance now has a dispersion, i.e. a specific relationship between angle and wavelength that is predefined by the materials and layer thicknesses of the respective layer/layer system 12.1 of such a sensor 12. A small reflection at an SPR sensor and BSW sensor can be observed. A displacement of the minimum of the reflection is observed as the measured signal. This displacement takes place along a vector S.

The light radiation should in this respect be directed onto the layer or onto the layer system 12.1 while taking account of the different angles for the different wavelengths $\lambda 1$, $\lambda 2$ and $\lambda 3$, where possible while observing total reflection conditions (TIR).

Metrological approaches for evaluating these resonances exist in i. monochromatic measurement with angle resolution, that is, observation of a section along the direction $S_\lambda(\theta)$ in FIG. 4; or
ii. spectrally resolved measurement at a fixed angle along the section $S_\theta(\lambda)$ in FIG. 4; or
iii. observation of intensity variations at a predefined angle and a predefined wavelength.

It is problematic that the measurement approaches (i) and (ii) are based on the fact that the wavelength spectrum or the angular spectrum is hugely restricted to be able to evaluate resonances that are as narrow as possible. Only the projection of the resonance shift onto the angular axis or wavelength axis in FIG. 4 is, however, thereby observed.

This effect could be reduced if an OLED 1 or an LED were to be used as the light source with a dispersion along the shift in resonance (vector S in FIG. 4). The can be achieved with the approach in accordance with FIG. 1 by an arrangement in accordance with FIG. 5. The sensor surface can there be illuminated with an extended spectrum of the required dispersion due to the dispersion of the light source. It must be noted that the angle between the OLED 1 as the light source and the sensor 9, 12 can be different from 90°. The detection takes place with a camera 9 with or without an objective analogously to FIG. 3a or 3b.

The arrangement in accordance with FIG. 5 has the disadvantage that different spectral components of different regions of the OLED 1 as the light source can be evaluated. Other components of the radiation field have to be suppressed by an absorbing diaphragm 15 under the layer system 12.1 of the sensor 12.

The above-described approach with the use of the camera 9 detecting with spatial resolution and wavelength resolution has the advantage that spectroscopic tests do not require a complex optoelectronic device (spectrometer) on the basis of a grid or prism. It is rather the case that a defined angle/wavelength relationship is predefined by the OLED 1 as the light source so that optical images with angular resolution automatically correspond to a spectral resolution.

An example with a sensor 12 is shown in FIG. 6. In this respect, light radiation is emitted from an OLED 1 received in a housing. In this respect, a part of the housing is configured as an optical element having a convex surface such that the light radiation that is emitted from the OLED 1 and that has been dispersed into individual wavelengths having different exit angles by the multilayer system 2 arranged thereon is incident onto a convex surface of a body 13 transparent for the light radiation as parallel light radiation and is thus focused on a layer 12.1 of an SPR sensor 12 or on a dielectric layer system 12.1 of a BSW sensor 12. The light radiation reflected divergently at the layer 12.1 is incident onto a second convex surface of the body 13 and is directed from there as parallel light radiation onto a detector array 9 such that the individual wavelengths and their respective intensity can be detected with spatial resolution and can be supplied to an evaluation.

FIG. 7 shows in schematic form an arrangement with two SPR sensors or BSW sensors 12, with the one shown at the top being able to be provided with a sample 8 and used for the measurement. The SPR sensor 12 arranged at the bottom can be used for a reference measurement. In this respect, the light radiation emitted from an OLED 1 and influenced by a multilayer system 2 is directed onto a layer 12.1 of an SPR sensor 12 such that light radiation of different wavelengths is incident at respectively different angles specific to the respective different wavelengths to excite surface plasmons. A sample 8 can be present on the layer 12.1.

Light radiation is again reflected at different angles analogously for the different wavelengths from the SPR sensor 12 irradiated in this manner and is directed to a camera 9 or to a detector array detecting with spatial resolution and wavelength resolution. An analytical evaluation of a sample 8 can be carried out using the signals thus detected.

A further example for a determination at samples 8 using an SPR sensor 12 is shown in FIG. 8a. In this respect, the light radiation emitted from an OLED 1 and split differently into individual light radiation by a multilayer system 2 enters into a body 13 transparent for the light radiation and is focused on a layer 12.1 on which a sample 8 can be arranged. This light radiation is reflected at the layer 12.1 and exits the body 13 as divergent light radiation before being incident onto a detector array 9 such that different wavelengths of the radiation are incident at different positions specific to the respective wavelength for a detection with spatial resolution and wavelength resolution. This arrangement has the advantage that the detector 9 is arranged perpendicular to the direction of propagation of the radiation to be detected.

In this example, an optical lens can also be arranged between the body 13 and the detector array 9 (FIG. 8b) and the reflected divergent light radiation is parallelized by it, whereby a perpendicular incidence of the light radiation onto the individual detectors of the detector array 9 can be achieved. This can, however, also be achieved with a convex surface of the body 13 from which the light radiation is reflected in the direction of the detector array 12 (FIG. 8c).

For an SPR sensor 12, a gold layer having a thickness in the range 45 nm to 55 nm can be used as the layer 12.1. The OLED 1 can emit light radiation in the wavelength range between 650 nm and 730 nm. In this respect, a multilayer system 2 can be used that can be formed alternately from $SiO_2$ and $Ta_2O_5$ layers. In this respect, two respective alternating layers are formed as a layer pair three times after one another on a substrate surface of the OLED 1. A start is made with a 263 nm thick $Ta_2O_5$ layer on which a 390 nm thick $SiO_2$ layer is formed. A layer of $Ta_2O_5$ having a thickness of 263 nm is formed on this layer stack and as the topmost layer an $SiO_2$ layer having a thickness of 169 nm is formed thereon.

FIG. 9 shows diagrams having angles of incidence of light radiation that can thus be achieved at different wavelengths and the reflection of a thin gold layer as the SPR sensor with angular resolution and wavelength resolution.

A design of an OLED 1 that can be used in an arrangement in accordance with the invention and having a multilayer system 2 is shown schematically in FIG. 10 such as can be used as a light source for a SPR sensor. In this respect, the multilayer system 2 is formed by way of example with layers of $SiO_2$ and $Ta_2O_5$. The layer system 12.1 of the SPR sensor 12 comprises a gold layer (not shown) of a thickness of approximately 50 nm. This sensor has the reflection with angular resolution and wavelength resolution shown at the left in FIG. 9. The relative intensities of light radiation that is incident at different angles of incidence in dependence on the respective wavelength after a (total) reflection that can accordingly be incident onto a detector array 9 at different positions, and that are shown in the diagram in FIG. 10 are obtained with the radiation field of an adapted OLED 1 (FIG. 9, right). The topmost curve extent corresponds to the observed light radiation without an SPR sensor layer, that is, with a pure total reflection of the radiation at the sensor position 12. If an SPR sensor layer 12.1 is covered by water as an aqueous solution, as the sample 8, the minimum of the observed intensity distribution shifts as the refractive index of said solution increases from approximately 68.5° up to approximately 72°. This shift of the minimum of the intensities can be observed since the respective wavelengths λ1, λ2 and λ3 are only emitted at different angles due to the dispersion of the light radiation energy (cf. vector S in FIG. 4). In the present example, for example, a multilayer system 2 of $Ta_2O_5$ and $SiO_2$ can be used that is designed in accordance with the structure $SiO_2{}^{169}|Ta_2O_5|\{SiO_2|Ta_2O_5\}^{3x}|$ substrate 5. In this respect, the topmost $SiO_2$ layer facing the OLED 1 is 169 nm thick; all the other $SiO_2$ layers have thicknesses of 390 nm and $Ta_2O_5$ layers have thicknesses of 263 nm.

With a BSW sensor 12, a thin film system can be used as the layer 12.1 in accordance with FIG. 11, middle, for the reflection, said system being formed by a 95 nm thick $TiO_2$ layer that is formed directly on the substrate of the OLED 1; by an $SiO_2$ layer formed thereabove and having a thickness of 300 nm; by a layer pair such as the first layer pair formed thereabove; and by a topmost layer of $TiO_2$ having a thickness of 15 nm. A sample 8, in particular a biological sample, can then be arranged on the last layer.

An OLED 1 in accordance with FIG. 11, right, that emits light radiation in the wavelength range between 550 nm and 685 nm that can be used in a BSW sensor 12 can be provided with a multilayer system 2 in which three pairs of $SiO_2$ layers and $Ta_2O_5$ layers having layer thicknesses of 87 nm for the $Ta_2O_5$ layers and 340 nm for the $SiO_2$-layers can be formed on a substrate surface. The first layer on the substrate surface comprises $Ta_2O_5$. A layer of $Ta_2O_5$ having a thickness of 87 nm is formed on the topmost layer of these three layer pairs and thereabove a layer of $SiO_2$ having a layer thickness of 138 nm as the topmost layer of the multilayer system 2.

The basic structure is shown in FIG. 11. In addition, a diagram is again shown that corresponds to FIG. 10. The topmost curve extent that has a steep gradient at an angle of incidence of approximately 60° corresponds to the observed spectrum of the OLED 1 after a total reflection without a multilayer system. If the reflection takes place at a BSW sensor covered with an aqueous solution (FIG. 11, middle), a local minimum of the reflection is observed in the range between 65° and 70° whose position shifts toward larger angles with an increasing optical refractive index of the aqueous solution analog to the SPR. The shift of the minimum of the detectable intensities at different wavelengths can thus also be used here for a spatially resolved determination.

The invention claimed is:

1. An arrangement for spatially resolved and wavelength-resolved detection of light radiation comprising at least one OLED (1) or LED from which light radiation having a plurality of different wavelengths λ1, λ2, λ3, . . . λn is emitted, a multilayer system (2) arranged between an electrode (3, 4) of an OLED (1) or of an LED and a substrate (5), wherein the multilayer system (2) is formed using layers arranged alternately above one another from a material having a higher and a lower optical refractive index n and light radiation from the at least one OLED (1) or LED having a plurality of different wavelengths λ1, λ2, λ3, . . . λn exits the multilayer system (2) such that light radiation having different wavelengths λ1, λ2, λ3, . . . n exits at defined angles, at least one detector array (9, 9.1) and an optical element (10, 11), wherein the optical element is an optical lens (10) or a prism (11) that is an integral component of a substrate (5) of the OLED (1) or of the LED and the optical lens (10) or the prism (11) is connected to the substrate (5) by means of an immersion fluid or is arranged at a spacing from the substrate (5) with a gap present there between, and the emitted light radiation is directed onto the detector array (9, 9.1) through a sample (8) at least partly transparent for the light radiation after at least a simple refraction at the optical element (10, 11) such that light radiation having wavelength λ1, λ2, λ3, . . . or λn is incident onto a respective detector element of the detector array (9, 9.1) and the detector elements of the detector array (9, 9.1) are arranged discretely from one another or at least one detector array (9, 9.1) and at least one sensor (12), wherein the at least one sensor (12) is at least one SPR sensor or BSW sensor (12) having a film or a thin film system (12.1) on which the sample (8) is arranged, and the emitted light radiation is directed onto the detector array (9, 9.1) after at least a simple reflection at the film or the thin film system (12.1) such that light radiation having wavelength λ1, λ2, λ3, . . . or λn is incident onto a respective detector element of the detector array (9, 9.1) and the detector elements of the detector array (9, 9.1) are arranged discretely from one another.

2. An arrangement in accordance with claim 1, characterized in that a microoptical surface structure (6) is formed on the surface of the substrate (5) at which the light radiation emitted from an OLED (1) or from an LED is incident or is present there.

3. An arrangement in accordance with claim 1, characterized in that light radiation of a respective angle is incident onto a correspondingly arranged defined detector element of the detector array (9, 9.1) such that the respective intensity of light radiation of the corresponding wavelengths λ1, λ2, λ3, . . . λn is measurable due to the properties of the light source.

4. An arrangement in accordance with claim 1, characterized in that a second detector array (9.1) is present that is preferably usable for a reference measurement.

5. An arrangement in accordance with claim 4, characterized in that two detector arrays (9, 9.1) are arranged with angular symmetry with respect to an axis or a plane.

6. An arrangement in accordance with claim 1, characterized in that a second multilayer system (2) is arranged above a second electrode (3 or 4) transparent for the emitted light radiation such that dispersed light radiation emitted from there at which different wavelengths λ1, λ2, λ3, . . . λn are emitted at different angles is incident onto at least one further detector array (9, 9.1).

* * * * *